United States Patent
Anelli et al.

(10) Patent No.: US 7,368,101 B2
(45) Date of Patent: *May 6, 2008

(54) PROCESS FOR THE PREPARATION OF IOPAMIDOL AND THE NEW INTERMEDIATES THEREIN

(75) Inventors: Pier Lucio Anelli, Milan (IT); Marino Brocchetta, Milan (IT); Giovanna Lux, Milan (IT); Enrico Cappelletti, Milan (IT)

(73) Assignee: Bracco Imaging S.p.A., Milan (IT)

( * ) Notice: Subject to any disclaimer, the term of this patent is extended or adjusted under 35 U.S.C. 154(b) by 177 days.

This patent is subject to a terminal disclaimer.

(21) Appl. No.: 11/316,559

(22) Filed: Dec. 21, 2005

(65) Prior Publication Data

US 2006/0106253 A1    May 18, 2006

Related U.S. Application Data

(63) Continuation of application No. 10/433,389, filed as application No. PCT/EP01/13939 on Nov. 29, 2001, now Pat. No. 7,034,183.

(30) Foreign Application Priority Data

Dec. 1, 2000    (IT)    .......................... MI2000A2601

(51) Int. Cl.
*A61K 49/04* (2006.01)
*C07C 233/00* (2006.01)
*C07D 407/00* (2006.01)

(52) U.S. Cl. ................... 424/9.454; 564/153; 549/370; 424/9.45

(58) Field of Classification Search ................ 564/153; 549/370; 424/9.454, 9.45
See application file for complete search history.

(56) References Cited

U.S. PATENT DOCUMENTS 4,001,323 A * 1/1977 Felder et al. ............... 564/153
4,352,788 A * 10/1982 Felder et al. ............ 424/9.454

FOREIGN PATENT DOCUMENTS

| CH | 616 403 | 3/1980 |
|---|---|---|
| CH | 627 653 | 1/1982 |
| WO | WO 00 50385 | 8/2000 |

OTHER PUBLICATIONS

Greene, T. and Wuts, P., Protective Groups in Organic Synthesis, 1999, John Wiley and Sons, p. 201-237.*
Felder, E. et al.; "Iopamidol", Analytical Profiles of Drug Substances, Academic Press, London, GB, vol. 17, pp. 115-154.
PCT International Search Report for PCT/EP01/13939 dated Mar. 19, 2002.
PCT International Preliminary Examination Report for PCT/EP01/13939 dated Oct. 2, 2002.

* cited by examiner

*Primary Examiner*—Michael G. Hartley
*Assistant Examiner*—Leah Schlientz
(74) *Attorney, Agent, or Firm*—Kramer Levin Naftalis & Frankel LLP

(57) ABSTRACT

A process for the preparation of (S)-N,N'-bis[2-hydroxy-1-(hydroxymethyl)ethyl]-5-[(2-hydroxy-1-oxo-propyl)amino]-2,4,6-triiodo-1,3-benzendicarboxamide (iopamidol) starting from 5-amino-N,N'-bis[2-hydroxy-1-(hydroxymethyl)ethyl]-2,4,6-triiodo-1,3-benzenedicarboxamide (II) which process comprises a) reacting the compound of formula (II) with a suitable protecting agent, to give a compound of formula (III) wherein R is a group of formula A or B wherein $R_1$ is a hydrogen atom, a $C_1 \div C_4$ straight or branched alkoxy group, $R_2$ is hydrogen, a $C_1 \div C_4$ straight or branched alkoy group and $R_3$ is a $C_1 \div C_4$ straight or branched alkyl group, a trifuoromethyl or a trichloromethyl group; b) acylating the amino group in position 5 of the intermediate compound of formula (III), by reaction with a (S)-2-(acetyloxy)propanoyl chloride to give a compound of formula (IV) wherein R is as defined above; and c) removing all the acyl groups present in the compound of formula (IV) under basic conditions, with prior cleavage of the cyclic protections of the hydroxy groups in the carboxamido substituents under acidic conditions, when R is a group of formula A carboxamido hydroxy groups under acidic conditions. The invention also refers to the new intermediates of formula (III) and (IV) wherein —R is a group A.

3 Claims, No Drawings

PROCESS FOR THE PREPARATION OF IOPAMIDOL AND THE NEW INTERMEDIATES THEREIN

RELATED APPLICATIONS

This application is a continuation of U.S. application Ser. No. 10/433,389, filed Dec. 22, 2003, now U.S. Pat. No. 7,034,183, which is the national stage filing of corresponding international application number PCT/EP01/13939, filed Nov. 29, 2001, which claims priority of Italian Application MI2000A002601, filed Dec. 1, 2000, all of which are hereby incorporated by reference in their entirety.

The present invention relates to a new process for the preparation of iopamidol (i.e. (S)-N,N'-bis[2-hydroxy-1-(hydroxymethyl)ethyl]-5-[(2-hydroxy-1-oxopropyl)amino]-2,4,6-triiodo-1,3-benzenedicarboxamide) starting from the corresponding 5-unsubstitued amino derivative and to the new intermediates obtained in said process.

BACKGROUND OF THE INVENTION (S)-N,N'-bis[2-hydroxy-1-(hydroxymethyl)ethyl]-5-[(2-hydroxy-1-oxopropyl)amino]-2,4,6-triiodo-1,3-benzenedicarboxamide of formula (I).

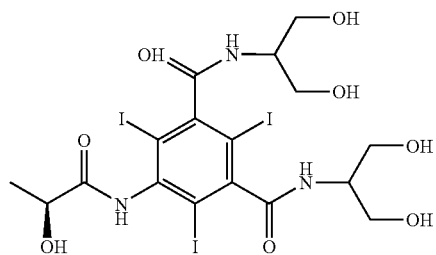

(I)

which is known as Iopamidol, is one of the most widely employed non-ionic radiographic contrast agents in the world.

It was first described in GB1472050, where its synthesis by the process outlined in the following Scheme has been reported:

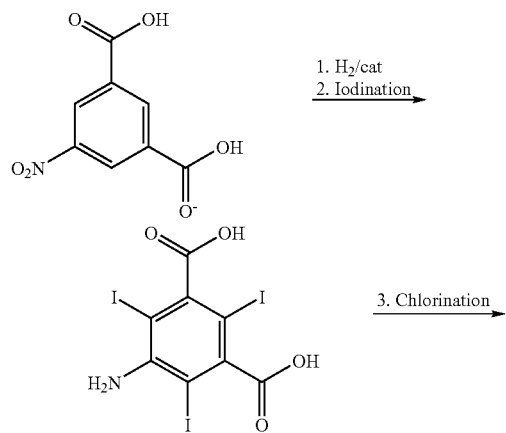

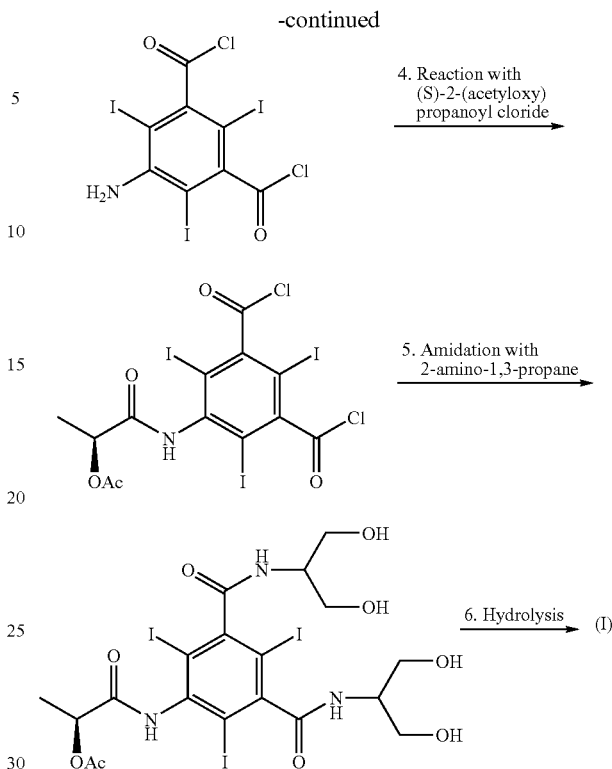

The above process, that is still widely employed industrially, has anyway several drawbacks.

One of them is the introduction of the protected chiral synton (S)-2-(acetyloxy)propanoyl on the 5-amino group at an early stage of the overall process, i.e. before the amidation with 2-amino-1,3-propanediol.

Just introducing this chiral group via reaction of the 5-amino-N,N'-bis[2-hydroxy-1-(hydroxymethyl)ethyl]-2,4,6-triiodo-1,3-benzenedicarboxamide with (S)-2-(acetyloxy) propanoyl chloride would lead to the preferential acylation of the more reactive hydroxy groups of the carboxamido substituents, thus causing remarkable wasting of expensive reactant.

WO 00/50385 has recently described a process for the preparation of polyhydroxy compounds (including i.a. iopamidol) comprising the step of deacylating, under acidic conditions, an acylated compound having the formula:

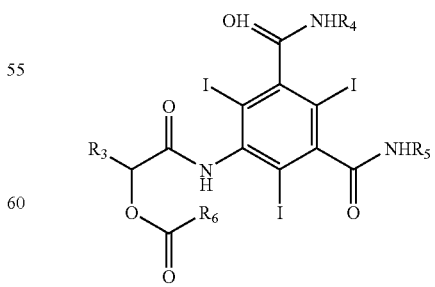

wherein $R_4$ and $R_5$ are optionally acylated dihydroxyalkyl groups, $R_6$ is alkyl and $R_3$ is i.a. a methyl group.

According to WO 00/50385 the acid used in this deacylation reaction is then removed by batch treatment with an acid scavenging resin; an aqueous solution of the thus obtained product is purified by passing through a non-ionic polymeric adsorbent resin; the eluate is concentrated to an oil; and the oil is crystallised from acetonitrile/ethanol or ethanol.

The above method is said to reduce racemization at the chiral carbon that—according to WO 00/50385—occurs whenever basic conditions are employed to remove the $R_6CO$— protecting group of the chiral substituent.

Examples of acyl groups reported in WO 00/50385 are formyl, acetyl, propanoyl, butanoyl, pivaloyl, pentanoyl, trifluoroacetyl, and benzoyl.

For iopamidol, WO 00/50385 describes the preparation of the starting acylated compound through introduction of the $R_6CO$— protected chiral substituent on the 5-amino group of a tetraester of the 5-amino-2,4,6-triiodo-1,3-benzenedicarboxamide. The isolated pentacylated product is then converted into iopamidol by the claimed process that requires deacylation under drastic acidic conditions. More particularly the actual conditions exemplified in WO 00/50385 for iopamidol are heating the pentacetyl derivative at the reflux temperature with hydrochloric acid in methanol for 30 hours.

SUMMARY OF THE INVENTION

It has now been found, and represents a first object of the present invention, that it is possible to carry out the deacylation of a pentacylated iopamidol, under basic conditions getting a final product, iopamidol, that has an extremely high optical purity.

Furthermore, it has been found that according to the process of the present invention it is not necessary to isolate the pentacylated product;

more particularly, it has been found that introducing the (S)-2-(acetyloxy)propanoyl substituent onto the 5-amino group of a N,N'-bis[2-hydroxy-1-(hydroxymethyl)ethyl]-2, 4,6-triiodo-1,3-benzenedicarboxamide wherein the hydroxy groups of the carboxamido substituents have been suitably acylated and then removing all the acyl groups under basic conditions without isolating the intermediate product, the overall process does proceed with very high yield.

Finally, it has been found that the process according to the present invention can be employed, with some modification, also when protection of the hydroxy groups of the carboxamido substituents is achieved by conversion of these groups into optionally 2-monosubstituted or 2,2-disubstituted N,N'-bis(1,3-dioxan-5-yl)carboxamides.

The new intermediates 5-amino-N,N'-bis(optionally 2-monosubstituted or 2,2-disubstituted-1,3-dioxan-2-yl)-2, 4,6-triiodo-1,3-benzenecarbox-amides (III) as well as the (S)-N,N'-bis(optionally 2-monosubstituted or 2,2-disubstituted-1,3-dioxan-2-yl)-5-[2-acetoxy-1-(oxopropyl)amino]-2,4,6-triiodo-1,3-benzenecarboxamides (IV) represent a further specific object of the present invention.

DETAILED DESCRIPTION OF THE PRESENT INVENTION

A first object of the present invention is therefore a process for the preparation of iopamidol (I)

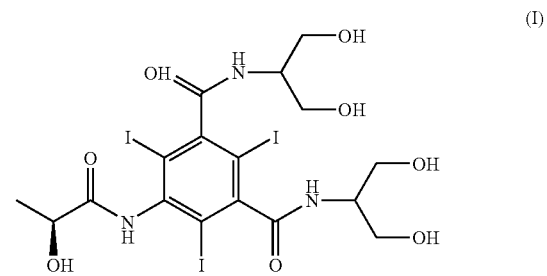

starting from the compound of formula (II)

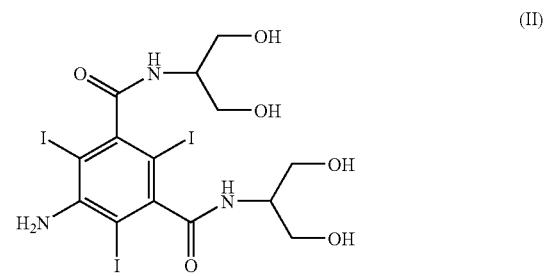

which process comprises a) reacting the compound of formula (II) with a suitable protecting agent, to give a compound of formula (III)

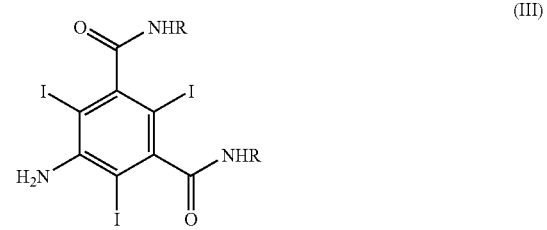

wherein —R is a group of formula A or B

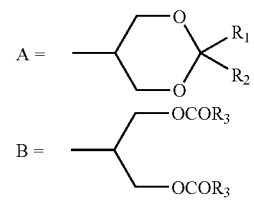

wherein $R_1$ is a hydrogen atom, a $C_1 \div C_4$ straight or branched alkyl group or a $C_1 \div C_4$ straight or branched alkoxy group, $R_2$ is a hydrogen atom, a $C_1 \div C_4$ straight or branched alkyl group or a $C_1 \div C_4$ straight or branched alkoxy group and $R_3$ is a $C_1 \div C_4$ straight or branched alkyl group, a trifluoromethyl, or a trichloromethyl group;

b) acylating the amino group in position 5 of the intermediate compound of formula (III), by reaction with a (S)-2-(acetyloxy)propanoyl chloride to give a compound of formula (IV)

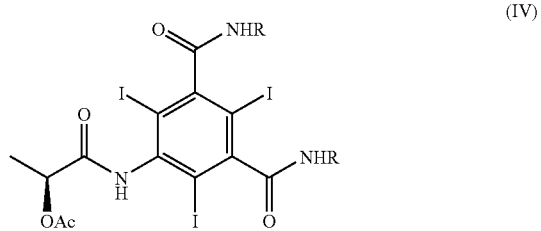

(IV)

wherein R is as defined above; and c) removing all the acyl groups present in the compound of formula (IV) under basic conditions, with prior cleavage of the cyclic protections of the hydroxy carboxamido substituents under acidic conditions when R is a group of formula A.

The compound of formula (II) is a known product and its preparation can be carried out by any of the known methods, such as those described in GB 1472050, CH 627653 or U.S. Pat. No. 5,278,311.

According to step a) of the process of the present invention the compound (II) is reacted with a compound which is suitably selected among aldehydes, ketones (possibly in the corresponding acetal or ketal related forms), orthoesters, or anhydrides, depending on the type of protecting group to be introduced.

For instance when —R in the compounds (III) represents a group of formula A, the compound (II) will be reacted with a di-($C_1$-$C_4$)alkoxy-methane when both $R_1$ and $R_2$ are hydrogen, with the suitably selected aldehydes or ketones of formula $R_1COR_2$ (possibly in the corresponding acetal or ketal related forms) in the presence of a small amount of a tri-($C_1$-$C_4$)alkyl orthoformate as dehydrating agent when $R_1$ is a hydrogen atom or a $C_1$÷$C_4$ straight or branched alkyl group and $R_2$ is a $C_1$÷$C_4$ straight or branched alkyl group or with orthoesters of formula $R_1C(R_2)_3$ when at least $R_2$ is an alkoxy group.

When, on the other hand, —R in the compounds (III) represents a group of formula B, said group is typically introduced by reacting the compound (II) with the suitably selected anhydride of formula $(R_3CO)_2O$.

When —R in the compounds (III) represents a group of formula A, preferred compounds are those wherein both $R_1$ and $R_2$ are $C_1$÷$C_4$ straight or branched alkyl groups; more preferred are those wherein both $R_1$ and $R_2$ are $C_1$÷$C_4$ straight alkyl groups; and even more preferred are those wherein both $R_1$ and $R_2$ are methyl.

Another group of preferred compounds (III) wherein —R represents a group A are those wherein $R_1$ is hydrogen and $R_2$ is a $C_1$÷$C_4$ straight alkoxy group.

When —R in the compounds (III) represents a group of formula B, preferred compounds are those wherein $R_3$ represents a $C_1$÷$C_4$ straight or branched, alkyl group; more preferred are those wherein $R_3$ represents a $C_1$÷$C_4$ straight alkyl group; even more preferred are those wherein $R_3$ is methyl.

The reaction of step a) is carried out in the presence of an organic solvent selected from the dipolar organic solvents, e.g. N,N-dimethylformamide, N,N-dimethylacetamide, and N-methyl-2-pyrrolidone, the inert aprotic organic solvents, and the mixtures thereof.

The reaction is carried out using at least the stoichiometric amount of the reactants but preferably at least a slight excess of the reactant introducing the protecting group with respect to the starting compound (II).

Needless to say that if a compound of formula (III) is desired wherein —R is a group A, at least two mol of the corresponding aldehyde or ketone (also in the form of the corresponding acetal or ketal) or orthoester have to be employed per mol of starting compound (II); while when a compound (III) is desired wherein —R is a group B then at least four mol of the corresponding anhydride must be used. In both cases, however, at least a slight excess, e.g. at least an excess of about 5% by mol over the stoichiometric amount is typically employed, a molar excess of up to about 50% being preferred.

The reaction is typically carried out at room temperature but lower or higher temperatures may as well be employed. As an example, temperatures in the range of from about 5° C. to about 60° C. proved to be suitable for step a).

The introduction of the protecting group in step a) is preferably carried out under slightly different reaction conditions depending on the particular reactant employed. The person skilled in the art will be aware of these differences and will be able to optimise the reaction conditions on the basis of his personal knowledge.

As an example, when in the compound (III) —R is a group of formula A, then step a) in the above process will be preferably carried out in the presence of an acidic catalyst. More particularly the reaction will be preferably carried out in the presence of from about 0.1 to about 2 mol of an acid per mol of compound of formula (II). Suitable acids that can be employed in this step are for instance sulfuric acid, hydrochloric acid, methanesulfonic acid, p-toluenesulfonic acid, or carboxylic acids, such as formic acid, acetic acid, or propionic acid.

For the preparation of the most preferred compound of formula (III) wherein —R is an A group wherein $R_1$ and $R_2$ are both methyl groups, the preferred reactant is acetone in the presence of a small amount of a tri-($C_1$÷$C_4$)alkyl orthoformate or 2,2-dimethoxypropane, while for the preparation of the compounds of formula (III) wherein —R is an A group wherein $R_1$ is hydrogen and $R_2$ is a $C_1$÷$C_4$ straight alkoxy group, the preferred reactants are the corresponding tri-($C_1$÷$C_4$) straight alkyl orthoformates.

In the actual practice, in the above case, the reaction will be preferably carried out by dripping a mixture of an excess over the stoichiometric of the suitably selected ketone/ketal or orthoformate together with a catalytic amount, typically about 0.1 mol per mol of compound of formula (II), of a strong acid, preferably sulfuric or methanesulfonic acid, into a solution of the compound of formula (II) in a dipolar aprotic solvent, typically N,N-dimethylacetamide.

Once the reaction, that may take from few minutes to 30 hours to be complete, is over, the protected compound of formula (III) wherein —R is a group of formula A is isolated, through neutralisation of the acidic catalyst, precipitation of the desired compound (III) by the addition of a diluted (generally 3% by weight) solution of bicarbonate, and purification of the precipitate by crystallisation from ethanol and water.

On the other hand, when in the compound (III) —R is a group of formula B, then step a) in the above process will be preferably carried out in the presence of a catalyst. More particularly it will be generally carried out in the presence of a small catalytic amount (typically from $5\times10^{-4}$ to $5\times10^{-1}$ mol per mol of starting compound (II)) of 4-(dimethylamino)pyridine. The reaction solvent may be selected—as indicated above—among the dipolar aprotic organic solvents, the inert non hydroxylated organic solvents and the mixtures thereof. When —R is a group B, also weakly basic organic solvents, such as pyridine, may be employed.

In the actual practice the reaction to get the compounds of formula (III) wherein —R is a compound of formula B will be preferably carried out by dripping a mixture of an excess over the stoichiometric of the suitably selected anhydride $(R_3CO)_2O$ and a catalytic amount, typically from 0.01 to 0.1 mol per mol of compound of formula (II), of 4-(dimethylamino)pyridine in a solution of the starting compound of formula (III) in N,N-dimethylacetamide. The 4-(dimethylamino)pyridine may be added to the reaction mixture as such or supported on a resin.

Once the reaction, that typically may take from a couple of hours to one day, depending on the reaction conditions employed, is complete, the protected compounds of formula (III) wherein —R is a group of formula B are precipitated from the reaction mixture by dilution with water or/and ethanol and isolated by filtration.

Step b) in the overall process outlined above consists in the acylation reaction of the primary amino group of the compounds of formula (III), with at least 1 mol of (S)-2-(acetyloxy)propanoyl chloride to give the compounds of formula (IV).

The reaction is usually carried out in an inert dipolar aprotic solvent such as N,N-dimethylacetamide, N,N-dimethylformamide, 1-methyl-2-pyrrolidone and the like solvents and in presence of an acid.

Acids that can suitably be employed in step b) are for instance hydrohalic acid that can easily be introduced into the reaction mixture as the hydrohalide salts of the dipolar aprotic solvents employed, such as the N,N-dimethylacetamide hydrochloride or—preferably—by bubbling the anhydrous hydrogen chloride gas into the reaction mixture.

The acid is typically employed in an amount of from about 0.1 to about 0.4 mol per mol of product of formula (III).

The temperature for this step of the reaction is generally comprised between about 5 and about 60° C.

Preferably, however, the reaction is carried out at room temperature or a temperature slightly above room temperature (about 45-50° C.).

The reaction of step b) is typically complete in a time comprised between about 2 and about 20 hours, depending on the solvent employed and the reaction conditions adopted.

In the following step c) all the acyl groups which are present in the intermediate compound of formula (IV) are removed under basic conditions, with prior cleavage of the cyclic protections under acidic conditions when R is a group of formula A.

In particular when a compound (IV) is employed wherein —R is a group of formula A, the basic hydrolysis to remove the acetyl protecting group of the 5-[(2-hydroxy-1-oxopropyl)amino] is preceded by cleavage of the cyclic protections of the carboxamido hydroxy groups under acidic conditions.

When on the other hand a compound (IV) is employed wherein —R is a group of formula B, all the acyl groups, i.e., the acetyl protecting group of the 5-[(2-hydroxy-1-oxopropyl)amino] substituent as well as the four $R_3CO$-groups, are removed in one single step under basic conditions.

The basic hydrolysis is carried out typically in water or in a mixture of water and an organic solvent miscible therewith such as a $C_1 \div C_4$ straight or branched alkanol, or a dipolar aprotic organic solvent such as N,N-dimethylformamide, N,N-dimethylacetamide, 1-methyl-2-pyrrolidone, and the like solvents.

The pH of the reaction mixture is maintained between 10 and 11 by the addition of a strong inorganic base such as NaOH or KOH, typically as an aqueous solution thereof. The reaction is preferably carried out at room temperature but temperatures of from about 10° C. to about 60° C. proved to be useful.

As indicated above, when in the compound of formula (IV) —R is a group of formula A, the basic hydrolysis of the acetyl group has to be preceded by the cleavage of the cyclic protections of the hydroxy groups of the carboxamido substituents under acidic conditions.

This is easily achieved by the addition of a strong cation exchange resin, preferably Duolite C20MB, Amberlite IR120 or Amberjet 1200 (Rohm & Haas) or of an aqueous solution of a strong mineral acid, e.g. hydrochloric or sulfuric acid, to a solution of the compound of formula (IV) wherein —R is a group A, in water or in a mixture of water and an organic solvent miscible therewith such as a $C_1 \div C_4$ straight or branched alkanol, or a dipolar aprotic organic solvent such as N,N-dimethylformamide, N,N-dimethylacetamide, 1-methyl-2-pyrrolidone, and the like solvents.

The amount of acid required in this step is comprised between about 0.2 and about 0.4 mol of acid per mol of compound of formula (IV) wherein —R is a group A. The reaction is preferably carried out at a temperature slightly above room temperature, e.g. comprised between about 40° C. and about 55° C., and is typically complete in 2 to 5 hours depending on the reaction conditions employed.

The hydrolysis under basic conditions to yield the end iopamidol is then just obtained by adding an aqueous solution of NaOH or KOH directly thereto in such an amount to keep the pH between about 10 and about 11.

The isolation of the product of formula (I) from the basic aqueous solution thus obtained, is usually carried out by passing the solution on a system of ionic exchange resins and optionally through a nanofiltration unit, as described for example in U.S. Pat. No. 5,811,581 or EP-A-888,190, followed by crystallization of the product (I) from a lower alkanol, as described for instance in U.S. Pat. No. 5,571,941.

A further specific object of the present invention are the intermediate compounds of formula (III) and (IV), wherein —R is a group of formula A

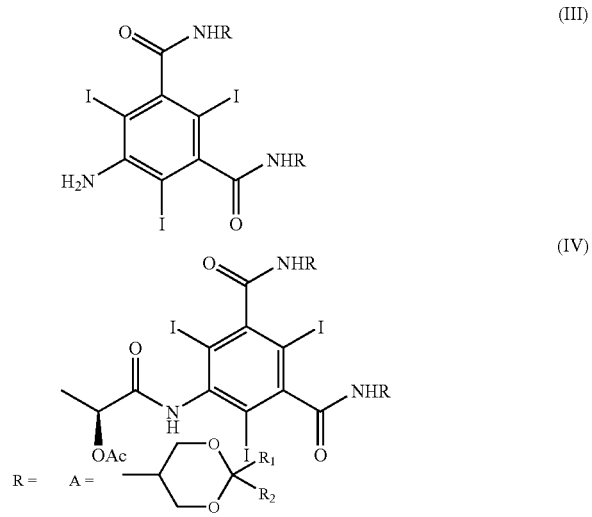

wherein $R_1$ is a hydrogen atom, a $C_1 \div C_4$ straight or branched alkyl group or a $C_1 \div C_4$ straight or branched alkoxy group, and $R_2$ is hydrogen, a $C_1 \div C_4$ straight or branched alkyl group or a $C_1 \div C_4$ straight or branched alkoxy group.

Preferred among the compounds of formula (III) and (IV) wherein —R is a group A are those wherein $R_1$ and $R_2$ are $C_1 \div C_4$ straight or branched alkyl groups; more preferred are those wherein both $R_1$ and $R_2$ are $C_1 \div C_4$ straight alkyl groups; and even more preferred are those wherein both $R_1$ and $R_2$ are methyl.

Another group of preferred compounds (III) and (IV) wherein —R represents a group A are those wherein $R_1$ is hydrogen and $R_2$ is a $C_1 \div C_4$ straight alkoxy group.

The following examples are only aimed at further illustrating the present invention in some of its preferred embodiments but should not be interpreted as a limitation to the scope thereof.

EXAMPLE 1

Preparation of 5-amino-N,N'-bis(2,2-dimethyl-1,3-dioxan-5-yl)-2,4,6-triiodo-1,3-benzenedicarboxamide ((III): —R=a group A wherein $R_1$ and $R_2$=methyl)

2,2-Dimethoxypropane (9.5 mL, 77.8 mmol) and 98% sulfuric acid (0.25 g, 2.6 mmol) are dripped into a 0.5 L vessel containing a solution of the compound of formula (II) (18.3 g, 25.9 mmol) (prepared as described in GB1472050) in dimethylacetamide (90 mL) stirred at room temperature. After 20 hours under stirring the solution is neutralised with $NaHCO_3$ and concentrated under vacuum. Acetone (250 mL) and 3% aq. $NaHCO_3$ (50 mL) are then added to the obtained oily residue and the solid is recovered by filtration and crystallized from 70% ethanol to give the compound of the title (13 g, 16.5 mmol after drying).

Yield: 64% The $^1$H-NMR, $^{13}$C-NMR, IR and MS are consistent with the indicated structure.

EXAMPLE 2

Preparation of 5-amino-N,N'-bis(2-ethoxy-1,3-dioxan-5-yl)-2,4,6-triiodo-1,3-benzenedicarboxamide ((III): —R=a group A wherein $R_1$ is hydrogen and $R_2$ is ethoxy)

Methanesulfonic acid (0.27 g, 2.8 mmol) and triethyl orthoformate (9.25 g, 62.4 mmol) are dripped in 1 hour into a solution of the compound of formula (II) (20 g, 28.4 mmol) (prepared as described in GB1472050) in N,N-dimethylacetamide (150 mL) stirred at 25° C. After 1 hour the solution is neutralised with $NaHCO_3$. The solvent is evaporated under vacuum and the oily residue is taken up with aq. 5% $NaHCO_3$ (300 mL).

The solid thus obtained is filtered and crystallized twice from 70% ethanol to afford the compound of the title (14.7 g, 18.7 mmol).

Yield: 66% The $^1$H-NMR, $^{13}$C-NMR, IR and MS are consistent with the indicated structure.

EXAMPLE 2 bis

Alternative Preparation of of 5-amino-N,N'-bis(2-ethoxy-1,3-dioxan-5-yl)-2,4,6-triiodo-1,3-benzenedicarboxamide ((III): —R=a group A wherein $R_1$ is hydrogen and $R_2$ is ethoxy)

Triethyl orthoformate (18.6 g, 125.5 mmol) is added over 3 min to a solution of the compound of formula (II) (40 g, 57 mmol) and methanesulfonic acid (0.55 g, 5.7 mmol) in N,N-dimethylacetamide (400 mL), stirred at room temperature. After 15 min, the reaction mixture is neutralized with 1M NaOH (5.7 mL, 5.7 mmol) and N,N-dimethylacetamide is distilled to give an oily residue. The latter is poured into 1% aq. $NaHCO_3$ causing the formation of a white precipitate that, after 15 h under stirring, is recovered by filtration, washed with $H_2O$ and dried. The solid is then suspended in absolute ethanol (600 mL), refluxed for 3 hours and allowed to cool to room temperature. The solid is recovered by filtration, washed with EtOH (30 mL) and dried to afford the compound of the title (40 g, 48.95 mmol) as a white solid.

Yield: 86%. The $^1$H-NMR, $^{13}$C-NMR, IR and MS are consistent with the indicated structure.

EXAMPLE 3

Preparation of N,N'-bis[2-acetyloxy-1-[(acetyloxy)methyl]ethyl]-5-amino-2,4,6-triiodo-1,3-benzenedicarboxamide ((III): —R is a group B where $R_3$ is methyl)

Acetic anhydride (9 mL, 95 mmol) is dripped into a suspension of the compound of formula (II) (7 g, 10 mmol) (prepared as described in GB1472050) in pyridine (40 mL) stirred at 25° C. After 3 hours, the solution obtained is added dropwise to deionized water (0.3 L) and the precipitate is recovered by filtration, washed with 5% acetic acid, then with deionized water, and finally dried under vacuum at the temperature of 40° C. for 12 hour to obtain the compound of the title (7.86 g, 9 mmol).

Yield: 90% The $^1$H-NMR, $^{13}$C-NMR, IR and MS are consistent with the indicated structure.

EXAMPLE 3 bis

Alternative Preparation of N,N'-bis[2-acetyloxy-1-[(acetyloxy)methyl]ethyl]-5-amino-2,4,6-triiodo-1,3-benzenedicarboxamide ((III): —R is a group B where $R_3$ is methyl)

The compound of formula (II) (1486 g, 2.1 mol) is loaded into a 10 L reactor containing N,N-dimethylacetamide (1.7 L) and 4-dimethylamino-pyridine (12.9 g) is then added thereto. Acetic anhydride (0.9 kg, 8.82 mol) is dripped therein over about 1 hour keeping the temperature below 30° C. The reaction mixture is stirred at room temperature for 20 hours, and then diluted with 96% ethanol (7.5 L). The precipitate is filtered, washed with 96% ethanol (2×1 L) and dried to give the compound of the title (1715 g, 1.96 mol).

Yield: 94% The $^1$H-NMR, $^{13}$C-NMR, IR and MS are consistent with the indicated structure.

EXAMPLE 4

Preparation of (S)-N,N'-bis[2-acetyloxy-1-[(acetyloxy)methyl]ethyl]-5-[(2-acetyloxy-1-oxopropyl)amino]-2,4,6-triiodo-1,3-benzenedicarboxamide (IV): —R is a group B wherein $R_3$ is methyl)

The compound prepared in Example 3 (11 g, 12,6 mmol) is dissolved in N,N-dimetylacetamide (200 mL) containing gaseous HCl (0.055 g, 1.5 mmol) and the solution is maintained at a temperature comprised between 15 and 17° C. (S)-2-(Acetyloxy)propanoyl chloride (4.75 g, 31.5 mmol) is dripped therein over 30 min. and the obtained reaction mixture is stirred at 23° C. for 20 hours. The solvent is then evaporated under vacuum and the oily residue is taken up with 4% aq. NaHCO$_3$ (250 mL). The obtained precipitate is recovered by filtration, washed and dried to yield the compound of the title (9.9 g, 10 mmol).

Yield: 80% The $^1$H-NMR, $^{13}$C-NMR, IR and MS are consistent with the indicated structure.

EXAMPLE 5

Preparation of (S)-N,N'-bis(2,2-dimethyl-1,3-dioxan-5-yl)-5-[(2-acetyloxy-1-oxopropyl)amino]—2,4,6-triiodo-1,3-benzenedicarboxamide ((IV): —R=a group A wherein R$_1$ and R$_2$ are methyl)

The compound prepared in Example 1 (15 g, 19 mmol) is dissolved in N,N-dimethylacetamide (80 mL) containing HCl gas (0.073 g, 2 mmol). (S)-2-(Acetyloxy)propanoyl chloride (8 g, 53 mmol) is dripped over 30 min into the obtained solution cooled to 15° C. After two hours at the same temperature, the reaction mixture is allowed to warm up to room temperature and stirred for additional 12 hours. The solvent is then evaporated under vacuum and the residue is taken up with 4% NaHCO$_3$ (130 mL). The solid obtained is filtered, washed and dried to give the compound of the title (14 g, 15,6 mmol).

Yield: 82% The $^1$H-NMR, $^{13}$C-NMR, IR and MS are consistent with the indicated structure.

EXAMPLE 6

Preparation of (S)-N,N'-bis[2-hydroxy-1-(hydroxymethyl)ethyl]-5-[(2-hydroxy-1-oxopropyl)amino]-2,4,6-triiodo-1,3-benzenedicarboxamide (I)

(S)-N,N'-Bis[2-acetyloxy-1-[(acetyloxy)methyl]ethyl]-5-[(2-acetyloxy-1-oxopropyl)amino]-2,4,6-triiodo-1,3-benzenedicarboxamide (4.9 g, 5 mmol) prepared in Example 4 is admixed with deionized water (30 mL) and methanol (30 mL). The suspension is warmed to 50° C., then 2M NaOH (12.8 mL) is dripped therein over a period of 4 hours, keeping the pH of the mixture in the range of from 10 to 11. The solution is purified on ion exchange resins columns and the neutral eluate thus obtained is concentrated under vacuum and the residue is crystallized from ethanol to give the compound of the title (2.8 g, 3.6 mmol)

Yield: 72%. $[\alpha]_{436}^{20}$=−5.15 (40% H$_2$O). The $^1$H-NMR, $^{13}$C-NMR, IR and MS are consistent with the indicated structure.

EXAMPLE 7

Alternative Preparation of (S)-N,N'-bis[2-hydroxy-1-(hydroxymethyl)ethyl]-5-[(2-hydroxy-1-oxopropyl)amino]-2,4,6-triiodo-1,3-benzenedicarboxamide (I)

0.2 M HCl (15 mL) is added to a solution of (S)-N,N'-bis(2,2-dimethyl-1,3-dioxan-5-yl)-5-[(2-acetyloxy-1-oxopropyl)amino]-2,4,6-triiodo-1,3-benzenedicarboxamide (9 g, 10 mmol) prepared as described in the Example 5, in methanol (60 mL), and the obtained mixture is stirred at 50° C. for 2 hours, and then cooled to 40° C. 1M NaOH (14 mL) is then dripped therein over a period of 2 hours to keep the pH between 10.5 and 11.

After two hours, the reaction mixture is cooled to room temperature and purified on ionic exchange resins. The neutral eluate thus obtained, is concentrated and the residue obtained is crystallized from ethanol (80 mL). The solid is filtered and dried to give the compound of the title (I) (7 g, 9 mmol).

Yield: 90% The $^1$H-NMR, $^{13}$C-NMR, IR and MS are consistent with the indicated structure.

EXAMPLE 8

Alternative Preparation of (S)-N,N'-bis[2-hydroxy-1-(hydroxymethyl)ethyl]-5-[(2-hydroxy-1-oxopropyl)amino]-2,4,6-triiodo-1,3-benzenedicarboxamide (I)

5-Amino-N,N'-bis(2,2-dimethyl-1,3-dioxan-5-yl)-2,4,6-triiodo-1,3-benzenedicarboxamide prepared as in Example 1, is reacted as described in Example 5. The (S)-N,N'-bis(2,2-dimethyl-1,3-dioxan-5-yl)-5-[(2-acetyloxy-1-oxopropyl)amino]-2,4,6-triiodo-1,3-benzenedicarboxamide obtained from the reaction is not isolated, but directly deprotected according to the method described in Example 7 above to give the compound of the title.

Yield: 74%. The $^1$H-NMR, $^{13}$C-NMR, IR and MS are consistent with the indicated structure.

EXAMPLE 9

Alternative Preparation of (S)-N,N'-bis[2-hydroxy-1-(hydroxymethyl)ethyl]-5[(2-hydroxy-1-oxopropyl)amino]-2,4,6-triiodo-1,3-benzenedicarboxamide (I)

(S)-2-(Acetyloxy)propanoyl chloride (16.5 g, 110 mmol) is added, over a period of 20 min, to a stirred solution of N,N'-bis[2-acetyloxy-1-[(acetyloxy)methyl]ethyl]-5-amino-2,4,6-triiodo-1,3-benzenedicarboxamide (53.3 g, 61.1 mmol) in N,N-dimethylacetamide (75 mL) while keeping the temperature of the reaction mixture below 30° C. An additional amount of (S)-2-(acetyloxy)propanoyl chloride (0.9 g, 6.0 mmol) is added after 24 and 30 hours and the reaction mixture is stirred at the same temperature for further 15 hours. The reaction mixture is then concentrated to half volume and diluted with a 1:1 mixture of water/methanol (360 mL). The resulting suspension is heated to 45° C. and 2M NaOH (225 mL, 450 mmol) is added over 30 min. After 2 h the hydrolysis is complete, the solution is concentrated to half volume, extracted with CH$_2$Cl$_2$ (6×100 mL) and loaded onto two ion exchange resin columns (Dowex® C350, H$^+$ form, 200 mL; Relite® MG1, OH— form, 160 mL) that are eluted with water. The eluate is evaporated and the solid residue (49 g) thus obtained is crystallized from ethanol (450 mL). The recovered solid (40.5 g) is dissolved in H$_2$O (400 mL) and the solution loaded onto an Amberlite® XAD-16.00 resin column (160 mL) that is eluted with water. The eluate is evaporated and the residue dried to afford Iopamidol (40.0 g, 51.5 mmol) as a white solid.

Yield: 84% $[\alpha]_{436}^{20}$=−5.17 (40% H$_2$O).

EXAMPLE 10

Alternative Preparation of (S)-N,N'-bis[2-hydroxy-1-(hydroxymethyl)ethyl]-5-[(2-hydroxy-1-oxopropyl)amino]-2,4,6-triiodo-1,3-benzenedicarboxamide (I)

(S)-2-(Acetyloxy)propanoyl chloride (16.5 g, 110 mmol) is added, over 20 min, to a stirred solution of N,N'-bis[2-acetyloxy-1-[(acetyloxy)methyl]ethyl]-5-amino-2,4,6-triiodo-1,3-benzenedicarboxamide (53.3 g, 61.1 mmol) in N,N-dimethylacetamide (75 mL) while keeping the temperature of the reaction mixture below 30° C. A further amount of (S)-2-(acetyloxy)propanoyl chloride (0.9 g, 6.0 mmol) is added after 24 and 30 hours and the reaction mixture is stirred at the same temperature for additional 15 hours. 5M NaOH (90 mL, 450 mmol) is dripped over a period of 2 hours into the reaction mixture vigorously stirred at 45° C. After two hours the mixture is concentrated under vacuum and reintegrated with additional N,N-dimethylacetamide (200 mL). After two hours at room temperature the resulting suspension is filtered and the solid washed with N,N-dimethylacetamide (2×20 mL). The mother liquors, combined with the washings, are concentrated to an oily residue, which is diluted with water (200 mL) and nanofiltered. The retentate is loaded onto an Amberlite® XAD-16.00 resin column (160 mL) that is eluted with water. The eluate is concentrated and loaded onto two ion exchange resin columns (Dowex® C350 15 mL, Relite® MG1 10 mL). The eluate is concentrated and the solid residue is crystallized from ethanol to afford Iopamidol (41.2 g, 53 mmol).

Yield: 87% $[\alpha]_{436}^{20}=-5.19$ (40% $H_2O$).

The invention claimed is:

1. Process for the preparation of (S)-N,N'-bis[2-hydroxy-1-(hydroxymethyl)ethyl]-5-[(2-hydroxy-1-oxopropyl) amino]-2,4,6-triiodo-1,3-benzenedicarboxamide of formula (I)

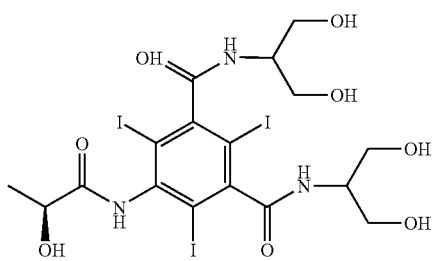

starting from the compound of formula (II)

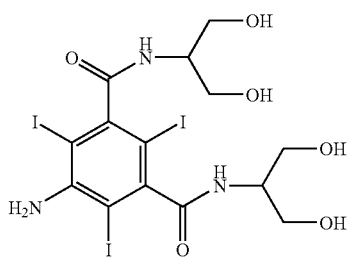

said process comprising:

a) reacting the compound of formula (II) with a suitable protecting agent, to give a compound of formula (III)

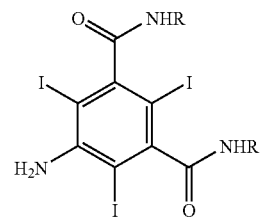

wherein —R is a group of formula A or B

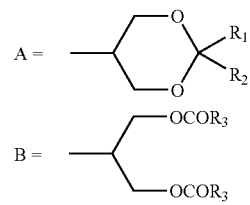

wherein $R_1$ is a hydrogen atom, a $C_1 \div C_4$ straight or branched alkyl group or a $C_1 \div C_4$ straight or branched alkoxy group, $R_2$ is hydrogen, a $C_1 \div C_4$ straight or branched alkyl group or a $C_1 \div C_4$ straight or-branched -alkoxy group and $R_3$ is a $C_1 \div C_4$ straight or branched alkyl group, a trifluoromethyl or a trichloromethyl group;

b) acylating the amino group in position 5 of the intermediate compound of formula (III), by reaction with a (S)-2-(acetyloxy)propanoyl chloride to give a compound of formula (IV)

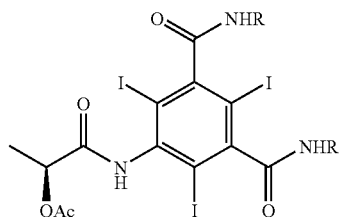

wherein R is as defined above; and c) removing all the acyl groups present in the compound of formula (IV) under basic conditions, with prior cleavage of the cyclic protection under acidic conditions when R is a group of formula A;

wherein there is no isolation step of the compound of formula (IV) before step c.

2. Process for the preparation of (S)-N,N'-bis[2-hydroxy-1-(hydroxymethyl)ethyl]-5-[(2-hydroxy-1-oxopropyl) amino]-2,4,6-triiodo-1,3-benzenedicarboxamide of formula (I)

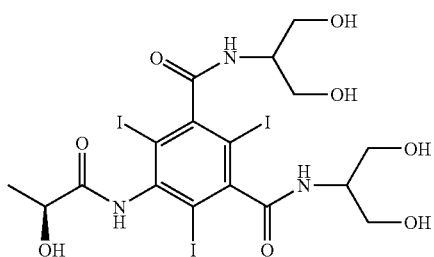

starting from the compound of formula (II)

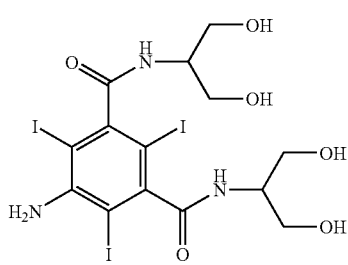

said process consisting of:
a) reacting the compound of formula (II) with a suitable protecting agent, to give a compound of formula (III)

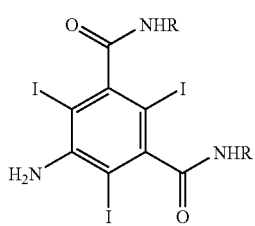

wherein —R is a group of formula A or B

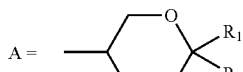

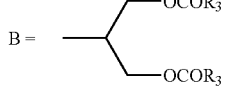

wherein $R_1$ is a hydrogen atom, a $C_1 \div C_4$ straight or branched alkyl group or a $C_1 \div C_4$ straight or branched alkoxy group, $R_2$ is hydrogen, a $C_1 \div C_4$ straight or branched alkyl group or a $C_1 \div C_4$ straight or-branched -alkoxy group and $R_3$ is a $C_1 \div C_4$ straight or branched alkyl group, a trifluoromethyl or a trichloromethyl group;
b) acylating the amino group in position 5 of the intermediate compound of formula (III), by reaction with a (S)-2-(acetyloxy)propanoyl chloride to give a compound of formula (IV)

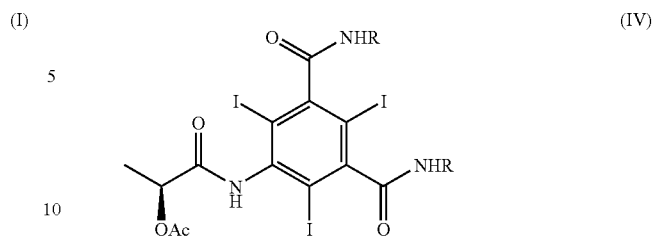

wherein R is as defined above; and
c) removing all the acyl groups present in the compound of formula (IV) under basic conditions, with prior cleavage of the cyclic protection under acidic conditions when R is a group of formula A.

3. Process for the preparation of (S)-N,N'-bis[2-hydroxy-1-(hydroxymethyl)ethyl]-5-[(2-hydroxy-1-oxopropyl) amino]-2,4,6-triiodo-1,3-benzenedicarboxamide of formula (I)

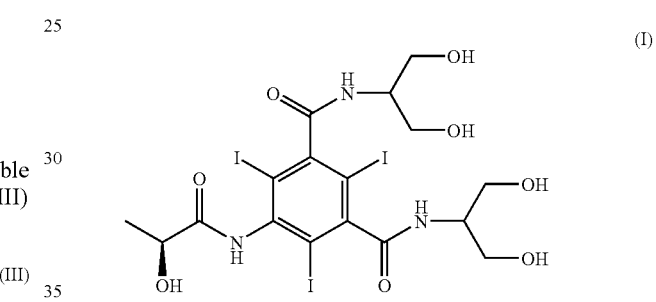

starting from the compound of formula (II)

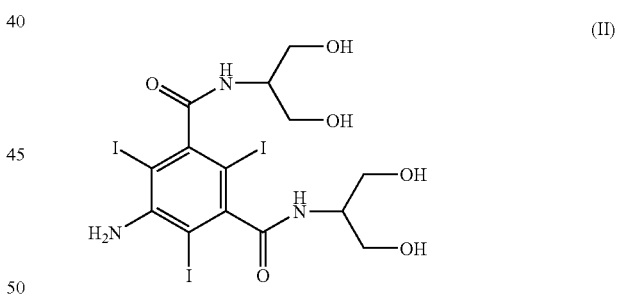

said process consisting essentially of:
a) reacting the compound of formula (II) with a suitable protecting agent, to give a compound of formula (III)

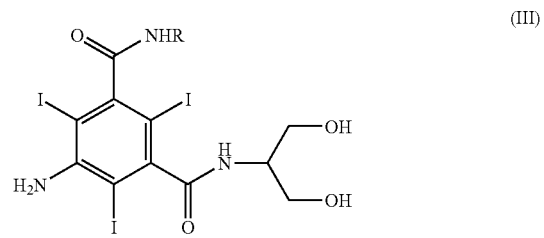

wherein —R is a group of formula A or B

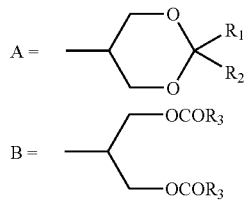

wherein $R_1$ is a hydrogen atom, a $C_1 \div C_4$ straight or branched alkyl group or a $C_1 \div C_4$ straight or branched alkoxy group, $R_2$ is hydrogen, a $C_1 \div C_4$ straight or branched alkyl group or a $C_1 \div C_4$ straight or-branched -alkoxy group and $R_3$ is a $C_1 \div C_4$ straight or branched alkyl group, a trifluoromethyl or a trichioromethyl group;

b) acylating the amino group in position 5 of the intermediate compound of formula (III), by reaction with a (S)-2-(acetyloxy)propanoyl chloride to give a compound of formula (IV)

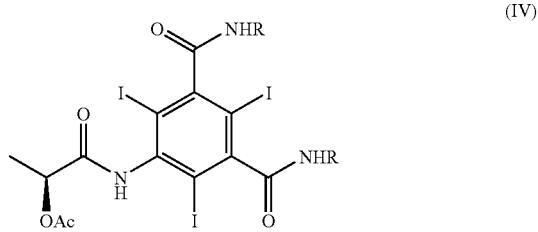

(IV)

wherein R is as defined above; and (c) removing all the acyl groups present in the compound of formula (IV) under basic conditions, with prior cleavage of the cyclic protection under acidic conditions when R is a group of formula A.

* * * * *

UNITED STATES PATENT AND TRADEMARK OFFICE
CERTIFICATE OF CORRECTION

PATENT NO. : 7,368,101 B2  Page 1 of 1
APPLICATION NO. : 11/316559
DATED : May 6, 2008
INVENTOR(S) : Anelli et al.

It is certified that error appears in the above-identified patent and that said Letters Patent is hereby corrected as shown below:

In claim 3, formula (III) (column 16, lines 56-65) should read:

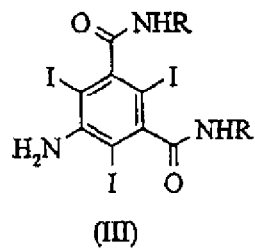

(III)

Signed and Sealed this

Thirtieth Day of June, 2009

JOHN DOLL
*Acting Director of the United States Patent and Trademark Office*